United States Patent
Petrig

(10) Patent No.: US 8,190,228 B2
(45) Date of Patent: May 29, 2012

(54) DOPPLER VELOCIMETRY OF RETINAL VESSELS AND APPLICATION TO RETINAL VESSEL OXIMETRY

(76) Inventor: Benno L. Petrig, Bloomington, IN (US)

( * ) Notice: Subject to any disclaimer, the term of this patent is extended or adjusted under 35 U.S.C. 154(b) by 1053 days.

(21) Appl. No.: 12/005,055

(22) Filed: Dec. 20, 2007

(65) Prior Publication Data

US 2008/0306364 A1    Dec. 11, 2008

Related U.S. Application Data

(60) Provisional application No. 60/876,088, filed on Dec. 20, 2006.

(51) Int. Cl.
*A61B 5/1455* (2006.01)
(52) U.S. Cl. ........................................ 600/340
(58) Field of Classification Search .................. 600/318, 600/323, 340
See application file for complete search history.

(56) References Cited

U.S. PATENT DOCUMENTS

| | | | | |
|---|---|---|---|---|
| 4,166,695 A | * | 9/1979 | Hill et al. | 600/504 |
| 4,877,322 A | * | 10/1989 | Hill | 600/323 |
| 5,106,184 A | * | 4/1992 | Milbocker | 600/558 |
| 5,240,006 A | * | 8/1993 | Fujii et al. | 600/476 |
| 5,776,060 A | * | 7/1998 | Smith et al. | 600/340 |
| 6,728,561 B2 | * | 4/2004 | Smith et al. | 600/323 |

\* cited by examiner

*Primary Examiner* — Eric Winakur
(74) *Attorney, Agent, or Firm* — Forrest Collins, Esq.; Forrest L. Collins Law Offices, LLC

(57) ABSTRACT

A new model based on ray tracing is developed to estimate power spectral properties in laser Doppler velocimetry of retinal vessels and to predict the effects of laser beam size and eccentricity as well as absorption of laser light by oxygenated and reduced hemoglobin. There is described the model and show that it correctly converges to the traditional rectangular shape of the Doppler shift power spectrum, given the same assumptions, and that reduced beam size and eccentric alignment cause marked alterations in this shape. The changes in the detected total power of the Doppler-shifted light due to light scattering and absorption by blood can also be quantified with this model and may be used to determine the oxygen saturation in retinal arteries and veins. The potential of this approach is that it uses direct measurements of Doppler signals originating only from moving red blood cells. The invention opens new avenues for retinal vessel oximetry.

9 Claims, 5 Drawing Sheets

DOPPLER VELOCIMETRY OF RETINAL VESSELS AND APPLICATION TO RETINAL VESSEL OXIMETRY

CROSS-REFERENCE

This application claims the benefit of U.S. provisional patent application 60/876,088 filed 20 Dec. 2006. The subject matter of U.S. provisional patent application 60/876,088 filed 20 Dec. 2006 is incorporated by reference in its entirety.

BACKGROUND OF THE INVENTION

1. Field of the Invention

The purpose of this invention is to permit determinations regarding blood.

2. Description of the Art Practices

The reader is referred to the following articles and publications:

1. C. E. Riva, B. Ross, and G. B. Benedek, "Laser Doppler measurements of blood flow in capillary tubes and retinal arteries," Invest. Opthalmol. 11, 936-944 (1972).
2. G. T. Feke and C. E. Riva, "Laser Doppler measurements of blood velocity in human retinal vessels," J. Opt. Soc. Am. 68 (4), 526-531 (1978).
3. C. E. Riva, G. T. Feke, B. Eberli, and V. Benary, "Bidirectional LDV system for absolute measurement of blood speed in retinal vessels," Appl. Opt. 18, 2301-2306 (1979).
4. C. E. Riva, J. E. Grunwald, S. H. Sinclair, and B. L. Petrig, "Blood velocity and volumetric flow rate in human retinal vessels," Invest. Opthalmol. Vis. Sci. 26, 1124-1132 (1985).
5. B. L. Petrig and C. E. Riva, "Retinal laser Doppler velocimetry: towards its computer-assisted clinical use," Appl. Opt. 27, 1126-1134 (1988).
6. E. Logean, L. F. Schmefterer, and C. E. Riva, "Velocity profile of red blood cells in human retinal vessels using confocal scanning laser Doppler velocimetry," Laser Phys. 13, 45-51 (2003).
7. B. L. Petrig and L. Follonier, "New ray tracing model for the estimation of power spectral properties in laser Doppler velocimetry of retinal vessels," ARVO Abstract (2005).
8. S. Wolfram, *Mathematica Book*, 5th ed. (Wolfram Media, Inc., 2003).
9. D. U. Fluckiger, R. J. Keyes, and J. H. Shapiro, "Optical autodyne detection: theory and experiment," Appl. Opt. 26, 318-325 (1987).
10. C. E. Riva, B. L. Petrig, and J. E. Grunwald, "Retinal blood flow," in *Laser-Doppler blood flowmetry*, A. P. Shepherd and P. A. Oberg, eds., pp. 349-383 (Kluwer Academic Publishers, 1989).
11. J. B. Lastovka, "Light mixing spectroscopy and the spectrum of light scattered by thermal fluctuations in liquids," Ph.D. thesis, Massachusetts Institute of Technology (1967).
12. C. E. Riva and G. T. Feke, "Laser Doppler velocimetry in the measurement of retinal blood flow," in *The Biomedical Laser: Technology and Clinical Applications*, L. Goldman, ed., pp. 135-161 (Springer, N.Y., New York, N.Y., USA, 1981).
13. O. W. van Assendelft, Spectrophotometry of hemoglobin derivatives (C. C. Thomas, Springfield, Ill., USA, 1990).
14. D. Schweitzer, M. Hammer, J. Kraft, E. Thamm, E. K"onigsd"orffer, and J. Strobel, "In vivo measurement of the oxygen saturation of retinal vessels in healthy volonteers," IEEE Trans. Biomed. Eng. 46, 1451-1465 (1999).
15. A. Ishimaru, *Wave Propagation and Scattering in Random Media*, vol. II (Academic Press, New York, 1978).
16. C. E. Riva, J. E. Grunwald, and B. L. Petrig, "Laser Doppler measurement of retinal blood velocity: validity of the single scattering model," Appl. Opt. 24, 605-607 (1985).
17. A. Harris, R. B. Dinn, L. Kagemann, and E. Rechtman, "A review of methods for human retinal oximetry," Ophthal. Surg. Las. Im. 34, 152-164 (2003).
18. F. C. Delori, "Noninvasive technique for oximetry of blood in retinal vessels," Appl. Opt. 27, 1113-1125 (1988).
19. B. Khoobehi, J. M. Beach, and H. Kawano, "Hyperspectral imaging for measurement of oxygen saturation in the optic nerve head," Invest. Opthalmol. Vis. Sci. 45, 1464-1472 (2004).
20. Optical Absorption of Hemoglobin by Scott Prahl, Oregon Medical Laser Center http://omlc.ogi.edu/spectra/hemoglobin/index.html.
21. Tabulated Molar Extinction Coefficient for Hemoglobin in Water 7 Pages http://omlc.ogi.edu/spectra/hemoglobin/summary.html.

Oxygen supply to the retina from the retinal and choroidal circulations at normal and increased arterial oxygen tensions, C. T. Dollery, C. J. Bulpitt, and Eva M. Kohner Volume 8 Number 8 pages 588-594 (1969).

The reader is further referred to U.S. Pat. No. 4,425,924 issued to Riva, et al. on Jan. 17, 1984 describing a method for determining the speed of leukocytes in retinal capillaries comprises the steps of simulating, by means of a minicomputer system which includes a visual display, the motion of entoptically seen leukocytes in retinal capillaries; observing entoptically the motion of actual leukocytes in the retinal capillaries of the subject's own eye; and comparing the appearances and motions of the visual display and the actual leukocytes. Apparatus for performing such a method comprises a minicomputer, a graphic display, and a display—processor interface. The reader is further referred to U.S. Pat. No. 4,476,878 issued to Riva, et al. on Oct. 16, 1984 that is a division application of U.S. Pat. No. 4,425,924.

The reader is further referred to U.S. Pat. No. 5,900,928 issued to Riva, et al. on May 4, 1999 describing an apparatus is provided for the measurement of the velocity of blood flowing within a blood vessel of an eye wherein the apparatus includes a light source for producing a source beam of light and an optical element for applying the source beam of light to the blood vessel to permit the blood flowing within the blood vessel to scatter a portion of the source beam of light and produce bidirectional scattered beams. A detector system for detecting the bidirectional scattered beams provides signals representative of the scattered beams. The light source and the detector system are disposed in a confocal relationship. An output representative of the velocity of the blood flow velocity is produced in accordance with the signals. The light source and the detector system include respective pinholes wherein the respective pinholes are disposed in the confocal relationship. The blood vessel is conjugate with the respective pinholes of the light source and the detector system. The angle between the bidirectional scattered beams is determined and a measurement of blood flow velocity is determined according to the angle.

To the extent that the foregoing references are relevant to the present invention, they are herein specifically incorporated by reference. Certain portions of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

The article *Doppler velocimetry of retinal vessels and application to retinal vessel oximetry* by Benno L. Petrig and Lysianne Follonier 2005 OSA 26 Dec. 2005/Vol. 13, No. 26/OPTICS EXPRESS 10642 is specifically incorporated herein by reference.

SUMMARY OF THE INVENTION

Many diseases of the human eye as well as the human body in general are caused by insufficient blood flow, low oxygenation, and poor oxygen transfer from oxyhemoglobin. It is important to diagnose such conditions so that treatments may be developed to treat the condition. It is also desirable that the test methods employed to detect such conditions avoid invasive procedures wherever possible.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 (b) according to FIG. 1 shows a vessel axis is on x-axis with blood velocity vector pointing in the direction of the positive x-axis;

DETAILED DESCRIPTION OF THE INVENTION

Figure 1:
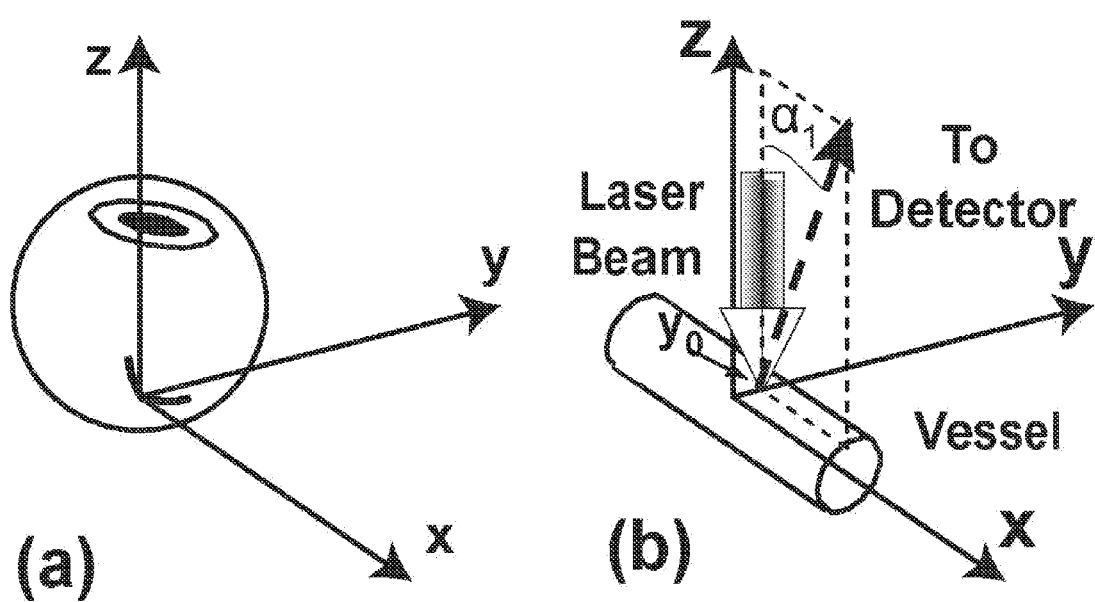
FIG. 1 (a) shows a Cartesian coordinate system for model calculations with origin at the retina.

Analysis of Doppler signals detected from red blood cells (RBCs) flowing in retinal vessels by laser Doppler velocimetry (LDV) was traditionally based on the following model. Assuming a parabolic blood velocity profile and uniform illumination of a cylindrical section of the vessel by laser light, one can show that the theoretical shape of the Doppler shift power spectrum (DSPS) is rectangular [1. C. E. Riva, B. Ross, and G. B. Benedek, "Laser Doppler measurements of blood flow in capillary tubes and retinal arteries," Invest. Opthalmol. 11, 936-944 (1972) and 2. G. T. Feke and C. E. Riva, "Laser Doppler measurements of blood velocity in human retinal vessels," J. Opt. Soc. Am. 68(4), 526-531 (1978) i.e., the DSPS is constant for all frequencies up to the "cutoff" frequency, fmax, which corresponds to the maximum velocity at the center of the vessel, Vmax.

This cutoff was determined either by visual inspection of the DSPS using a spectrum analyzer [3. C. E. Riva, G. T. Feke, B. Eberli, and V. Benary, "Bidirectional LDV system for absolute measurement of blood speed in retinal vessels," Appl. Opt. 18, 2301-2306 (1979) and 4. C. E. Riva, J. E. Grunwald, S. H. Sinclair, and B. L. Petrig, "Blood velocity and volumetric flow rate in human retinal vessels," Invest. Opthalmol. Vis. Sci. 26, 1124-1132 (1985), or automatically by a curve fitting algorithm using a computer [B. L. Petrig and C. E. Riva, "Retinal laser Doppler velocimetry: towards its computer-assisted clinical use," Appl. Opt. 27, 1126-1134 (1988].

Several factors contribute, however, to alter this theoretical shape. If the laser beam diameter is much smaller than the vessel size, as for example in a confocal system [6. E. Logean, L. F. Schmetterer, and C. E. Riva, "Velocity profile of red blood cells in human retinal vessels using confocal scanning laser Doppler velocimetry," Laser Phys. 13, 45-51 (2003)], only part of the blood column is illuminated, and thus, some streamlines are missed. The intensity profile may not be uniform but Gaussian, thus not all RBCs are illuminated equally. Absorption of light by hemoglobin and scattering by RBCs also cause non-uniformity of laser illumination, depending on the wavelength and the total path length in blood.

To quantify the relative contributions of all these factors and their combined effects on the DSPS, a new theoretical model has been developed, which allows the estimation of the power spectral shape more precisely using various geometrical and other parameters describing different configurations of the LDV paradigm [B. L. Petrig and L. Follonier, "New ray tracing model for the estimation of power spectral properties in laser Doppler velocimetry of retinal vessels," ARVO Abstract (2005)].

To describe this model in detail and apply it to predict the effects of varying relative laser beam versus retinal vessel size, eccentricity of beam intersection with the vessel, and differences in the absorption of laser light between oxy- and deoxyhemoglobin at various wavelengths. A potential application to retinal vessel oximetry is discussed.

The new LDV model consists of two main components, the blood vessel lumen containing the moving RBCs and the incident laser beam. The intersection of these two 'rods', i.e., the homogeneous collection of those RBCs that are illuminated by laser light, is defined as the measuring volume'. It is assumed that the detector 'sees' all the light coming towards it from the entire measuring volume and that the laser and detector are relatively far away from the point of measurement.

This model keeps track of the path length of the laser light inside the measuring volume to take into account light absorption by hemoglobin contained in RBCs as a function of distance traveled within the blood column. The laser wavelength is also taken into account because of the spectral differences in the absorption coefficient between oxy- and deoxyhemoglobin. Power spectral shapes can thus be predicted for various available laser lines using wavelengths located either at isobestic points (same absorption coefficient) or at points with a large difference in absorption coefficients.

Because of the complexity of the required model calculations, Mathematica 5 (Wolfram Research, Champaign, Ill., USA) is employed, which provides the tools to evaluate the non-linear relationships that apply in this model and to perform the calculations necessary for numerical integration [8].

In a first approximation, the human retina (and thus the portions of retinal arteries and veins outside the optic disc) can be thought of as lying on a sphere. The model uses a Cartesian coordinate system, whose origin is on this sphere at the 'point of measurement' (FIG. 1(a)), where the x-axis is tangential to the sphere and coincides with the blood vessel axis (FIG. 1(b)). The y-axis is also tangential to the sphere, thus the z-axis goes through its center.

FIG. 1. (a) shows Cartesian coordinate system for model calculations with origin at the retina. FIG. 1. (b) shows vessel axis is on x-axis with blood velocity vector pointing in the direction of the positive x-axis. The y-axis is tangential to the retina, z-axis goes through center of eye. Laser beam axis is in the direction of the negative z-axis intersecting the y-axis at eccentricity $y_0$ from the vessel axis. Detector axis lies in a plane parallel to the xz-plane at $y_0$ (dashed rhombus) and makes an angle $\alpha_1$ with the laser axis.

The blood vessel lumen is considered circular in this model. The positive x-axis is in the direction of the RBCs flowing through the vessel (FIG. 1(b)). The vessel radius is held constant in all calculations presented here (R=50 μm).

The velocity profile, assumed to be parabolic (laminar flow) and symmetric about the x-axis, is given by the following equation $$v(r)=(1-r^2/R^2)V_{max} \quad (1)$$

where r is the distance from the x-axis and Vmax is the centerline blood velocity.

Although the velocity profile normally can show temporal variation (especially in arteries, due to the cardiac cycle), this is not considered further in this model. It is assumed that blood flow pulsatility does not alter the spectral shapes, but affects only the scale of the Doppler shift frequency, as long as the profile remains parabolic and the scattering characteristics of the RBCs are constant within the range of velocity fluctuations during the heart beat.

The laser beam is modeled as parallel light at a wavelength $\lambda$ with a Gaussian beam intensity profile given by $$I_1(\rho)=I_0\exp(-2\rho^2/w^2) \quad (2)$$

where $\rho$ is the distance from the beam axis, $I_0=2P_0/(\pi w^2)$ is the on-axis laser beam intensity, $P_0$ is the total power of the incident beam, and w is the distance from the beam axis, at which the intensity falls to $1/e^2$. In the model, $P_0$ is a fixed value (unity) and the laser beam intensity profile is truncated at $I_1(\rho)=0$ w, (i.e., $/1(\rho)=0$ for $\rho>w$). So the total power in the beam is the same for all beam sizes.

The wave vector $\vec{k}_i$ of the incident laser beam is assumed to be parallel to the z-axis, and the laser axis is modeled to go through a point $y_0$ on the y-axis. This simplifies the calculation of the incident laser light intensity I(x, y, z) at any given point using Eq. (2).

The detector is located on an axis defined by the wave vector $k_s$, which goes through the same point $y_0$ where the laser axis intersects the y-axis. This axis also lies in a plane parallel to the xz-plane and makes an angle $\alpha_1(=10°)$ with the laser axis (FIG. 1(b)). The portion of the light scattered towards the detector coming from moving RBCs is very small compared to that coming from the static vessel wall, which is not Doppler-shifted and acts like a local oscillator that can be used for heterodyne mixing spectroscopy [D. U. Fluckiger, R. J. Keyes, and J. H. Shapiro, "Optical autodyne detection: theory and experiment," Appl. Opt. 26, 318-325 (1987) and 10. C. E. Riva, B. L. Petrig, and J. E. Grunwald, "Retinal blood flow," in *Laser-Doppler blood flowmetry*, A. P. Shepherd and P. A. Oberg, eds., pp. 349-383 (Kluwer Academic Publishers, 1989)]. In this model, the intensity of the local oscillator on the detector surface is assumed to be constant.

It is assumed a square-law detector that produces an output current, which is proportional to the square of the two interfering incident optical fields, integrated over the coherence area at the photocathode is employed. Thus the photocurrent is proportional to the intensity of the incident light.

The power spectral density function of this photocurrent, the DSPS, is then calculated following the procedure as described in detail elsewhere [12. C. E. Riva and G. T. Feke, "Laser Doppler velocimetry in the measurement of retinal blood flow," in *The Biomedical Laser: Technology and Clinical Applications*, L. Goldman, ed., pp. 135-161 (Springer, New York, N.Y., NY, USA, 1981)].

In this model it is considered only the so-called 'pseudo single backscattering' mode [9]. This means that the laser light eventually reaching the detector is thought to have undergone many forward scattering events without any change in the angle of $k_i$ (imparting no Doppler shift) and one single large-angle backscattering event in the direction of the detector, i.e., of wave vector $k_s$ (imparting a Doppler shift once).

But most of the incident light is in fact lost, because it is either scattered away from the detector by the RBCs or absorbed by hemoglobin. Because only a very small fraction $\gamma$ of the light incident at any given location within the measuring volume is scattered towards the detector, a large portion of the light $(1-\gamma)$ is lost due to scattering, which in whole blood is mostly forward. It is assumed here that this probability $\gamma$ is constant and uniform throughout the measuring volume.

The basic approach taken is to calculate the local intensity of the incident and backscattered laser light, along with the Doppler shift frequency, for an infinitesimal volume element placed at a given locus within the measuring volume. In its general form, the Doppler shift frequency at a radius r from the vessel axis is defined by the scalar product:

$$f(r)=(1/2\pi)[\vec{v}(r)\cdot(\vec{k}_s-\vec{k}_i)] \quad (3)$$

where $\vec{v}(r)$ is the blood velocity vector. For the scattering geometry used in this model and with $|\vec{k}_s|=|\vec{k}_i|=2\pi n/\pi$ this becomes a simple product:

$$f(r)=v(r)\sin(\alpha_1)n/\lambda \quad (4)$$

where n is the index of refraction of the flowing medium.

First an integration over all loci that produce the same Doppler shift, which yields one single point on the DSPS curve. In the model, this corresponds to RBCs moving at the same velocity in a "flow tube", which has a radius $r=(y^2+z^2)^{1/2}$ around the vessel axis and an infinitesimal annular "wall" of thickness dr. In general, for a nonuniform laser beam, this integral is not simply proportional to the circumference and length of this flow tube, but has to be evaluated for all loci, because the incident laser intensity varies with position around the annulus as well as along the tube.

Thus, one must first calculate the total intensity scattered towards the detector by the RBCs flowing in the portion of flow tube of radius r that is "cut out" by the truncated laser:

$$I_{sc}(r)=\gamma \int_{x_{min}}^{x_{max}} \int_{y_{min}(x)}^{y_{max}(x)} I_1(x,y)l_{arc}(y,r)dy\,dx \quad (5)$$

where $I_1(x,y)$ is the local incident laser intensity. Variable $l_{arc}(y,r)$ is the local arc length of the flow tube annulus (at location y on a plane parallel to the yz-plane placed at x). It is calculated as $$l_{arc}(y,r)=[1+(dz/dy)^2]^{1/2}=[1+y^2/(r^2-y^2)]^{1/2}$$

The limits of the above double integral are defined by the circular shape of the laser, which may be smaller than the flow tube and placed eccentrically to the vessel axis. This integral cannot be evaluated analytically (because the limits contain one of the integration variables), but an equivalent integral was solved instead, using numerical integration and related methods of Mathematica [8].

In order to take into account light absorption, a calculation for each locus on the flow tube the path length of the incident ($d_i$) and scattered ($d_s$) light and apply the Beer-Lambert law $$I = I_1 \exp[-\mu_\alpha(\lambda) d];$$

with absorption coefficient $\lambda_\alpha(\lambda)$ and path length $d = d_i + d_s$, before and after the single backscattering event. With $d_s = d_i / \cos(\alpha_1)$ and for a small angle $\alpha_1$, there is obtained $d \approx 2d_i$, and Eq. (5) can be rewritten as $$I_{sc}(r) = \gamma \int_{x_{min}}^{x_{max}} \int_{y_{min}(x)}^{y_{max}(x)} I_1(x, y) \exp[-\mu_a(\lambda) d(y)] l_{arc}(y, r) \, dy \, dx \qquad (6)$$

where the total path length for loci above and below the xy-plane is given by:

$$d(y) = \begin{cases} 2[(R^2 - y^2)^{1/2} - (r^2 - y^2)^{1/2}] & z \geq 0 \\ 2[(R^2 - y^2)^{1/2} + (r^2 - y^2)^{1/2}] & z < 0 \end{cases} \qquad (7)$$

The complete spectrum of the scattered intensity is obtained by evaluating Eq. (6) for all r, but only to the extent that the corresponding points lie within the measuring volume defined above. Then the intensity spectrum of the light scattered by moving RBCs is converted from r-space to f-space (see [1] Appendix II) as follows:

$$I_{sc}(f) = \frac{\lambda R^2}{2n \sin(\alpha_1) V_{max}} \frac{I_{sc}(r)}{r} \qquad (8)$$

Finally, the DSPS (the Doppler-shifted portion of the detected photocurrent [10]) is obtained from $$DSPS(f) = \beta(\lambda)^2 S S_{lo} I_{lo} I_{SC}(f) \qquad (9)$$

where $\beta(\lambda)$ is the responsively of the photodetector. S is the illuminated photocathode area, $S_{lo}$ and $I_{lo}$ are the coherence area and the intensity of the local oscillator at the photocathode, respectively, which are held constant in the present model.

Figure 2:
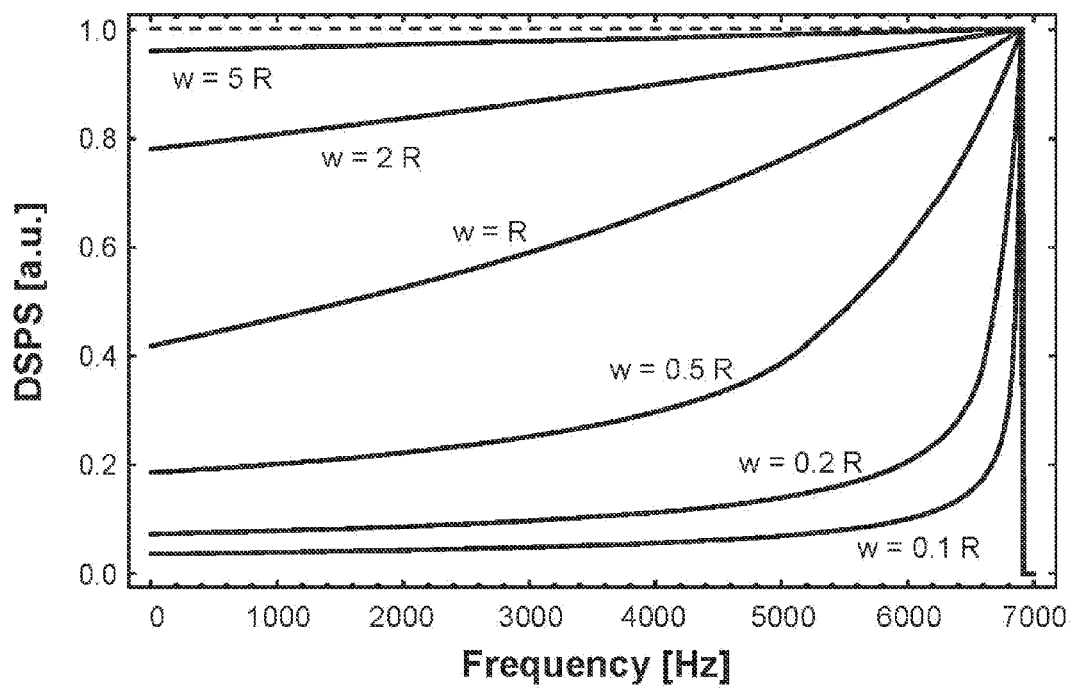
FIG. 2 are Model calculations of Doppler signal power spectral shapes in a round vessel.

The model is first validated by defining its parameters such that they approach the traditional LDV configuration. To achieve this, the laser beam radius is made much larger than the vessel radius (w=100 R), which results in all flow tubes being illuminated over approximately the same length. Vessel and laser axes intersect at the origin, and the laser intensity at each point is uniform, without taking into account absorption. FIG. 2 shows indeed the expected rectangular shape (dashed line).

In FIG. 2. model calculations of Doppler signal power spectral shapes in a round vessel (radius R=50 µm) are shown. Laser illumination (670 nm) is either uniform (traditional LDV, dashed line) or has a Gaussian shape with beam radii w=5, 2, 1, 0.5, 0.2 and 0.1 R. Laser beam and vessel axes are in the same plane, perpendicular to each other. Scattered beam angle: $\alpha_1 = 10°$.

The other curves of FIG. 2 show the power spectral shapes for laser beam radii of w=5, 2, 1, 0.5, 0.2 and 0.1 R. Vessel and laser axes still intersect at the origin, but now the laser intensity has a truncated Gaussian shape, as defined above. The DSPS curves are normalized for equal power at $f_{max}$. As the laser beam radius gets progressively smaller than the vessel radius, power is lost at the low frequency end of the DSPS, because the laser beam misses more and more of the outer streamlines.

Figure 3:
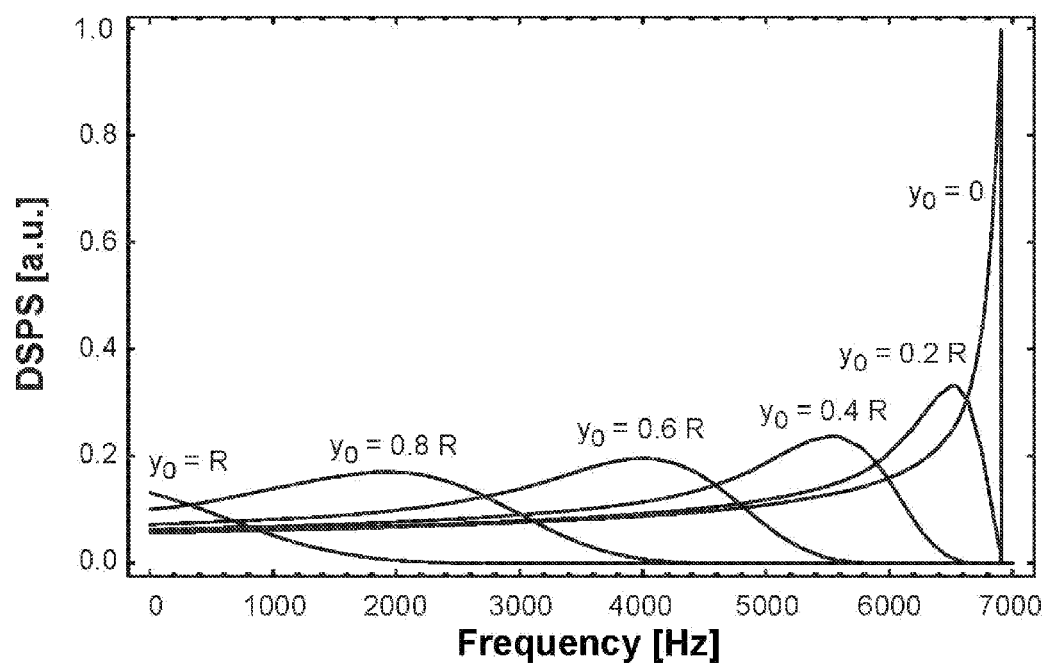
FIG. 3 sets forth power spectral shapes in a round vessel.

The effect of eccentric placement of a small laser beam on the vessel is shown in FIG. 3. It should be noted that there is a marked flattening in the shape of the DSPS with increasing eccentricity, not only a scaling of the frequency axis, as more and more of the streamlines near the center are missed.

Figure 4:
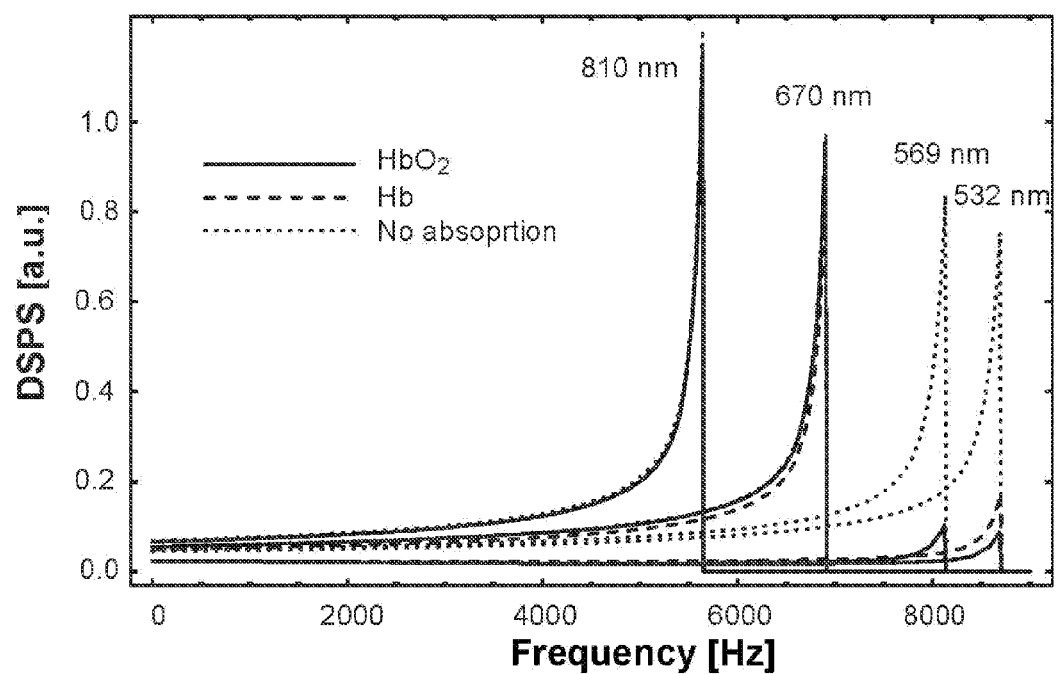
FIG. 4 sets forth of a second power spectral shapes in a round vessel.
Figure 5:
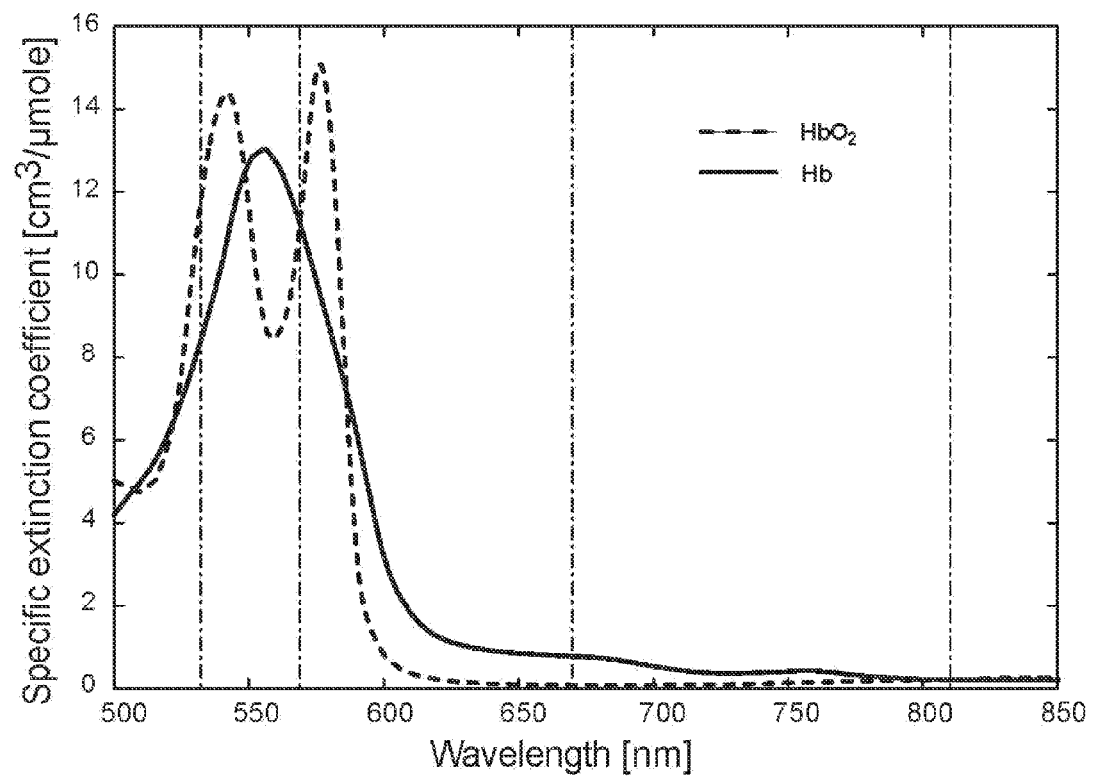
FIG. 5 shows specific absorption coefficient spectrum of oxy- and deoxyhemoglobin With more particular reference to the drawings the following is set forth.

FIG. 4 shows DSPS shapes for a small Gaussian laser beam (w=0.2 R) at various wavelengths ($\lambda$=532, 569, 670 and 810 nm). Three different absorption coefficients were modeled (none, oxy- and deoxyhemoglobin), for the latter two using the wavelength-dependent coefficients shown in FIG. 5. Note that absorption plays no or only a small role at the two longer wavelengths (810 and 670 nm), for which the model was calculated, regardless of oxygen saturation. At the shorter wavelengths (569 and 532 nm), the model predicts a considerable reduction in power at when absorption is taken into account. Furthermore, at 532 nm, the power for oxyhemoglobin is reduced to about half of that for deoxyhemoglobin. At the isobestic wavelength of 569 nm, the model predicts the same power reduction for oxy- and deoxyhemoglobin, as expected.

From FIG. 4, it is seen that at 532 nm the model predicts a total power under the DSPS curve for deoxy- and oxyhemoglobin of about 25% and 12.5%, respectively, when compared to the total power that would be predicted without absorption (dashed line). Since this total shifted power without absorption is unknown, the measured total Doppler-shifted power, Ps$h,\gamma$ must be calibrated in a different way to obtain the oxygen saturation (SO 2) of blood. A possible calibration procedure could be achieved as follows.

Again referring to FIG. 4, it is noted that the predicted total power of the shifted light at 810 or 670 nm is the same or very similar for oxy- and deoxyhemoglobin and that there is no or very little absorption compared to 532 nm. Therefore, the power of the shifted light measured, for example at 810 nm, represents a reference value (100%) for the measurements at 532 nm. Thus, one can calculate the ratio of total shifted power predicted for pure oxy- and deoxyhemoglobin, respectively.

$$k_0 = \frac{P_{HbO2 \cdot sh \cdot 532}}{P_{HbO2 \cdot sh \cdot 810}} \qquad (10)$$

$$k_1 = \frac{P_{Hb \cdot sh \cdot 532}}{P_{Hb \cdot sh \cdot 810}} \qquad (11)$$

Now, for a given mixture of the two pigments [$\alpha$ oxyhemoglobin, (1−$\alpha$) deoxyhemoglobin], the total shifted power measured at 532 nm, $P_{sh.532}$, will fall somewhere between those two end-points and, therefore, one can write $$P_{Sh.532} = \alpha P_{HbO2.sh.532} + (1-\alpha) P_{Hb.sh532} \qquad (12)$$

Exploiting the isobestic condition (same absorption coefficient for either pigment) one obtains $$P_{Sh.810} = P_{HbO2.sh.810} = P_{Hb.sh.810} \qquad (13)$$

and, thus, solving Eq. (12) for $\alpha$ and inserting Eqs. (10), (11) and (13), one obtains the following formula for $SO_2$ $$P_{Sh.810} = P_{HbO2.sh.810} = P_{Hb.sh.810} \qquad (14)$$

where $k_0$ and $k_1$ are the theoretical values taken from Eq. (10) and (11) of the LDV model, and $P_{sh.532}$, $P_{sh.810}$ are the measured values of total Doppler-shifted power at each wavelength (area under each DSPS).

Since the power of the two lasers incident on the vessel is likely not the same, the measured photodetector direct current (DC) could be used to compensate for this. The DC represents the non-shifted light scattered by the vessel wall, which is proportional to the incident laser power. Therefore, the power of the shifted light at 532 nm must be scaled by the ratio of the respective DC powers to adjust for uneven incident laser power.

$$SatO_2 = \alpha * 100\% = \frac{k_1 P_{Sh\cdot 810} - k_2 P_{Sh\cdot 532}}{(k_1 - k_0) P_{Sh\cdot 810}} * 100\% \quad (15)$$

where $k_2 = Pd_{c.810}/P_{dc.532}$.

This new model provides a basis for improving future LDV analysis algorithms and to study the effect of various model parameters to gain a better understanding of the LDV paradigm in retinal vessels, by comparing the theoretical shapes of the DSPS predicted by the model with those actually measured.

The model calculations shown here demonstrate that the shape of the DSPS differs markedly from a rectangle if a highly focused Gaussian laser beam is used, if the beam is not centered on the vessel and if absorption of light by the blood column is considered. The use of an eyetracking device would minimize the effects of eccentricities due to eye motion.

Some simplifying assumptions have been made to limit the already high complexity of the model presented here. With new generations of software it may become feasible to allow variations in additional parameters, such as asymmetric velocity profiles near vessel junctions or a noncircular vessel lumen that may be expected in retinal veins. And a detector aperture conjugated to the retinal plane could be added to the model.

In the present model, γ, the probability of single backscattering of light towards the detector by moving RBCs, was held constant in Eqs. (5) and (6). A spatially non-uniform distribution or a wavelength dependency of this probability, γ(x, y, z, λ) could be introduced with a future extension of the model and placed inside the double integral. This could include a possible dependency on RBC velocity, as shown for reflectometry [14. D. Schweitzer, M. Hammer, J. Kraft, E. Thamm, E. Königsdörffer, and J. Strobel, "In vivo measurement of the oxygen saturation of retinal vessels in healthy volunteers," IEEE Trans. Biomed. Eng. 46, 1451-1465 (1999)].

In general, the Beer-Lambert law for light propagation in a tissue layer of thickness d states that the total light attenuation by absorption and scattering is given by $I(d)=I_1 \exp(-[\mu_a+\mu_s] d)$, where μa and μs are the absorption and scattering coefficients, respectively. In whole blood, where the mean free pathlength between two scattering events is comparable to the RBC size, any detected Doppler-shifted light must have undergone many scattering events, and light is scattered predominantly in the forward direction (mean cosine of the scattering angle >0.99 [15. A. Ishimaru, *Wave Propagation and Scattering in Random Media*, vol. II (Academic Press, New York, 1978).].

Therefore, it is assumed for the purpose of this model that all of the incident light at any given point inside the vessel lumen is scattered forward at zero angle from $k_i$, except for a very small portion γ that is scattered towards the detector in a single backscattering event [16. C. E. Riva, J. E. Grunwald, and B. L. Petrig, "Laser Doppler measurement of retinal blood velocity: validity of the single scattering model," Appl. Opt. 24, 605-607 (1985).]. All remaining incident light (1−γ) that has completely traversed the blood column is considered lost for detection, accounting for all the scattering losses at that point. After having been backscattered towards the detector, that portion of the light is taken to be scattered forward again, at zero angle from $k_s$. Because γ is assumed to be very small compared to the absorption coefficient, one does not consider this attenuation due to backscattering inside the integral of Eq. (6) as done for absorption. This could, however, be taken into account more precisely in a future extension of the model, as stated above.

Changes in the backscattering properties of unshifted light from the vessel wall (e.g., as a function of location: front vs. back, center vs. sides) were not modeled explicitly here. The intensity of the local oscillator $l_{lo}$ at the detector is presently included in Eq. (9) as a constant.

One could possibly model the tube of the vessel wall in a similar fashion as it was done with the RBCs inside the vessel and determine the variations of the local oscillator intensity as a function of wavelength and location within the vessel wall. However, to introduce it into the model, i.e., from Eq. (9) inside the integrals of Eqs. (5) and (6), this intensity would have to be expressed with respect to the locus of the Doppler-shifted light intensity, $I_{lo}$ (x, y, z, λ) which with it is associated.

In the data shown here, the DSPS curves for the different absorption coefficients were normalized to the DSPS curve without light absorption in a medium size retinal vessel of 100 μm diameter. The results show that compared to the 670 nm laser, the signal-to-noise ratio at 532 nm needs to be approximately 10 times higher, which should be achievable with a higher laser power delivered over a shorter time. Using an eye-tracking device and turning the probing laser on for only a few seconds would allow measurements with a minimum of light exposure. If needed, light exposure could be further reduced by measuring sequentially, turning only one probing laser on at a time.

Even though 670 nm is not an isobestic point, FIG. 4 shows that the total shifted power for oxy- and deoxyhemoglobin differs only by a few percents, because the absorption coefficient is already very small compared to 532 nm. Therefore, as a compromise, a 670 instead of 810 nm laser may be used as a reference for Eq. (15).

If the scattering properties at the above wavelengths (532 vs. 810 or 670 nm) turn out to be too different for the calibration by the DC to be accurate (i.e., if γ or the local oscillator depends strongly on wavelength), then an isobestic point close to 532 nm, for example 569 or even 548 nm, could be chosen instead. In that case, it should be noted that the total shifted power for oxyhemoglobin at 569 and 548 nm is similar to that at 532 nm (FIG. 4), requiring a comparable signal-to-noise ratio of the detector system.

Inexpensive diode lasers are available today at 532, 670 and 810 nm, but not yet at 548 or 569 nm. However, electro-optics technology is advancing rapidly and new laser lines may soon become available near 569 or 548 nm. Or a tunable, although more expensive, laser may be employed instead.

Previously developed techniques of retinal vessel oximetry (for a review see [17. A. Harris, R. B. Dinn, L. Kagemann, and E. Rechtman, "A review of methods for human retinal oximetry," Ophthal. Surg. Las. Im. 34, 152-164 (2003).] were mostly based on ocular fundus reflectance measurements, either using discrete wavelengths [18. F. C. Delori, "Noninvasive technique for oximetry of blood in retinal vessels," Appl. Opt. 27, 1113-1125 (1988)], or by spectrometry over the whole visible spectrum [14, and B. Khoobehi, J. M. Beach, and H. Kawano, "Hyperspectral imaging for measurement of oxygen saturation in the optic nerve head," Invest. Opthalmol. Vis. Sci. 45, 1464-1472 (2004).].

The potential of retinal vessel oximetry based on Doppler-shifted light is that this light necessarily originates from RBCs moving within the blood column, which could open new avenues for retinal vessel oximetry.

From the above description of the invention, those skilled in the art will perceive improvements, changes and modifications. Such improvements, changes and modifications within the skill of the art are intended to be covered by the appended claims.

What is claimed is:

1. A method for determining the oxyhemoglobin content in a blood vessel of a mammalian subject comprising:
    directing a first incident beam of laser light into an ocular blood vessel having an ocular blood vessel outer wall and an ocular blood vessel inner wall such that said first incident beam of laser light has a radius that is less than the radius of the ocular blood vessel inner wall;
    measuring the Doppler shift power spectrum of the scattered laser light from said first incident beam with a detector;
    directing a second incident beam of laser light at a different wavelength than said first incident beam into the same ocular blood vessel having an ocular blood vessel outer wall and an ocular blood vessel inner wall such that said second incident beam of laser light has a radius that is less than the radius of the ocular blood vessel inner wall;
    measuring the Doppler shift power spectrum of the scattered laser light from said second incident beam with a detector;
    comparing the total Doppler shift power of said scattered beam of laser light from said first incident beam with the total Doppler shift power of said scattered laser light from said second incident beam to obtain a differential between the total Doppler shift power of said two scattered beams of laser light of different wavelength;
    choosing the wavelength of the first said laser light to be at an isobestic point and the wavelength of the second said laser light to be at a point where the extinction coefficient of oxy- and deoxyhemoglobin is maximally different or
    choosing the wavelength of the first said laser light to be at a point where the extinction coefficient of oxy- and deoxyhemoglobin is maximally different and the wavelength of the said second laser light to be at a point where the extinction coefficient of oxy- and deoxyhemoglobin is maximally different in the opposite direction; and,
    correlating said differential to a reference value of oxyhemoglobin content, determined from a theoretical model of a blood vessel of a similar size, with that of the measured ocular blood vessel; and,
    determining the oxyhemoglobin content in a blood vessel based on results of the correlating step.

2. The method according to claim 1 wherein the wavelength of the incident beam of laser light is between 500 nm and 1500 nm.

3. The method according to claim 1 wherein ocular blood vessel is a retinal vein or venule.

4. The method according to claim 1 wherein ocular blood vessel is a retinal artery or arteriole.

5. The method according to claim 1 wherein ocular blood vessel is a retinal capillary.

6. The method according to claim 1 wherein the reference value of oxyhemoglobin content for a blood vessel is determined by other non-invasive or invasive means.

7. A method for determining the flow of oxygenated blood through a blood vessel of a mammalian subject comprising:
    directing a first incident beam of laser light into an ocular blood vessel having an ocular blood vessel outer wall and an ocular blood vessel inner wall such that said first incident beam of laser light has a radius that is less than the radius of the ocular blood vessel inner wall;
    measuring the Doppler shift power spectrum of the scattered laser light from said first incident beam with a detector;
    directing a second incident beam of laser light at a different wavelength than said first incident beam into the same ocular blood vessel having an ocular blood vessel outer wall and an ocular blood vessel inner wall such that said second incident beam of laser light has a radius that is less than the radius of the ocular blood vessel inner wall;
    measuring the Doppler shift power spectrum of the scattered laser light from said second incident beam with a detector;
    comparing the total Doppler shift power of said scattered beam of laser light from said first incident beam with the total Doppler shift power of said scattered laser light from said second incident beam to obtain a differential between the total Doppler shift power of said two scattered beams of laser light of different wavelength;
    choosing the wavelength of the said first laser light to be at an isobestic point and the wavelength of the second said laser light to be at a point where the extinction coefficient of oxy- and deoxyhemoglobin is maximally different or
    choosing the wavelength of the first said laser light to be at a point where the extinction coefficient of oxy- and deoxyhemoglobin is maximally different and the wavelength of the said second laser light to be at a point where the extinction coefficient of oxy- and deoxyhemoglobin is maximally different in the opposite direction; and,
    correlating said differential to a reference value of oxyhemoglobin content, determined from a theoretical model of a blood vessel of a similar size, with that of the measured ocular blood vessel;
    thereby determining the oxyhemoglobin content in a blood vessel,
    determining the volume of blood flowing through the same ocular vessel by the average Doppler shift of the scattered laser light of said scattered beam moving across the inner lumen of the ocular vessel;
    multiplied by the cross section of the same ocular vessel; and
    determining the product of the oxyhemoglobin content and the volumetric blood flow in a blood vessel; and,
    determining the flow of oxygenated blood through a blood vessel based on results of the correlating step.

8. A method according to claim 7 further comprising determining the amount of oxygen delivered to ocular tissue by determining the difference in oxygenated blood flow in corresponding ocular vessels between the arterial and venous side of the vasculature, or between different ocular vessel branch orders.

9. A method according to claim 7 further comprising determining the amount of oxygen delivered to ocular tissue by determining the oxygen content of blood and the difference in oxygenated blood flow in corresponding ocular vessels between the arterial and venous side of the vasculature, or between different ocular vessel branch orders, using a light source, which has a spectrum within the range of 500 to 1500 nm.

* * * * *